United States Patent [19]

Schneider

[11] 4,122,097

[45] Oct. 24, 1978

[54] THROMBOXANE B DIALKYLACETAL INTERMEDIATES

[75] Inventor: William P. Schneider, Kalamazoo, Mich.

[73] Assignee: The Upjohn Company, Kalamazoo, Mich.

[21] Appl. No.: 830,541

[22] Filed: Sep. 6, 1977

Related U.S. Application Data

[60] Division of Ser. No. 716,473, Aug. 20, 1976, Pat. No. 4,070,384, which is a continuation-in-part of Ser. No. 676,894, Apr. 14, 1976, Pat. No. 4,018,804.

[51] Int. Cl.$^2$ .......................... C07C 69/66; C11C 3/00
[52] U.S. Cl. ..................................... 260/405; 260/408; 260/410.5; 260/410.9 R; 560/183; 560/184; 560/185

[58] Field of Search ....................... 560/183, 184, 185; 260/405

[56] References Cited

PUBLICATIONS

Derwent Abstract 68629X/36 US 3976678 24. 08. 761.
Derwent Abstract 88674X/47 US 3991-087, 09/11/76.

Primary Examiner—Paul J. Killos
Attorney, Agent, or Firm—Robert A. Armitage

[57] ABSTRACT

The present specification provides novel intermediates and novel processes for the synthesis of various side chain and skeletal analogs of Thromboxane $B_2$ ($11\beta$-homo-11a-oxa-PGF$_{2\alpha}$). These analogs are particularly and especially useful as reproductive cycle control agents.

1 Claim, No Drawings

THROMBOXANE B DIALKYLACETAL INTERMEDIATES

The present invention is a divisional application of Ser. No. 716,473, filed Aug. 20. 1976, now issued as U.S. Pat. No. 4,070,384; which is a continuation-in-part of Ser. No. 676,894, filed Apr. 14, 1976, issued as U.S. Pat. No. 4,018,804 on Apr. 19, 1977.

The present invention relates to processes and intermediates for Thromboxane B compounds for which the essential material constituting a disclosure therefor is incorporated by reference herein from U.S. Pat. No. 4,020,173, issued Apr. 26, 1977 and U.S. Pat. No. 4,070,384, issued Jan. 24, 1978.

I claim:

1. A thromboxane intermediate of the formula

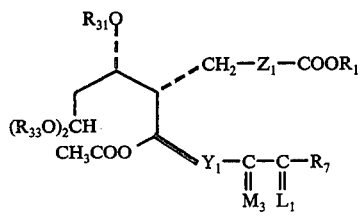

wherein $R_{31}$ is a hydroxy hydrogen replacing group;
wherein Z is
  (1) cis—CH=CH—CH$_2$—(CH$_2$)$_g$—CH$_2$—,
  (2) cis—CH=CH—CH$_2$(CH$_2$)$_g$—CF$_2$—,
  (3) cis—CH$_2$—CH=CH—(CH$_2$)$_g$—CH$_2$—,
  (4) —(CH$_2$)$_3$—(CH$_2$)$_g$—CH$_2$—,
  (5) —(CH$_2$)$_3$—(CH$_2$)$_g$—CF$_2$—, or
  (6) —CH$_2$—O—CH$_2$—(CH$_2$)$_g$—CH$_2$—,
wherein $g$ is one, 2, or 3;
  wherein $R_1$ is alkyl of one to 12 carbon atoms, inclusive, cycloalkyl of 3 to 10 carbon atoms, inclusive, aralkyl of 7 to 12 carbon atoms, inclusive, phenyl, phenyl substituted with one or two chloro, fluoro, or alkyl of one to 4 carbon atoms, inclusive, or a pharmacologically acceptable cation;
wherein $Y_1$ is trans—CH=CH— or —CH$_2$CH$_2$—;
wherein $M_3$ is

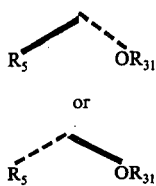

or wherein $R_5$ is hydrogen or methyl and $R_{31}$ is a hydroxyhydrogen replacing group;
wherein $L_1$ is

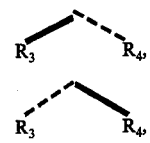

or a mixture of

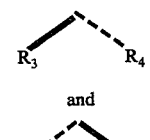

and

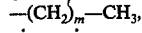

wherein $R_3$ and $R_4$ are hydrogen, methyl, or fluoro, being the same or different with the proviso that one of $R_3$ and $R_4$ is methyl only when the other is hydrogen or methyl; and
wherein $R_7$ is
  —(CH$_2$)$_m$—CH$_3$,
wherein $m$ is one to 5, inclusive; and
wherein $R_{33}$ is alkyl of one to 5 carbon atoms, inclusive.

* * * * *

UNITED STATES PATENT OFFICE
CERTIFICATE OF CORRECTION

Patent No. 4,122,097          Dated  October 24, 1978

Inventor(s) William P. Schneider

It is certified that error appears in the above-identified patent and that said Letters Patent are hereby corrected as shown below:

In the References Cited, "Derwent Abstract 68629X/36" should read -- Derwent Abstract 68619X/36 --;

Column 1, line 30, "wherein Z is" should read -- wherein $Z_1$ is --;
Column 1, line 32, "(2) cis-$CH=CH-CH_2(CH_2)_g-CF_2$-" should read -- (2) cis-$CH=CH-CH_2-(CH_2)_g-CF_2$- --.

Signed and Sealed this

Sixteenth Day of January 1979

[SEAL]

Attest:

RUTH C. MASON
Attesting Officer

DONALD W. BANNER
Commissioner of Patents and Trademarks